United States Patent [19]

Decker et al.

[11] Patent Number: 5,306,820
[45] Date of Patent: Apr. 26, 1994

[54] PROCESS FOR THE PREPARATION OF ENANTIOMERICALLY PURE SUBSTITUTED (QUINOLIN-2-YL-METHOXY)PHENYLA-CETIC ACIDS

[75] Inventors: Matthias Decker; Klaus-Helmut Mohrs, both of Wuppertal; Siegfried Raddatz, Köln, all of Fed. Rep. of Germany

[73] Assignee: Bayer Aktiengesellschaft, Leverkusen, Fed. Rep. of Germany

[21] Appl. No.: 866,707

[22] Filed: Apr. 10, 1992

[30] Foreign Application Priority Data

Apr. 17, 1991 [DE] Fed. Rep. of Germany ....... 4112533

[51] Int. Cl.⁵ .................. C07D 215/00; C07D 215/12; C07D 215/16
[52] U.S. Cl. .................... 546/153; 546/154; 546/155; 546/156; 546/168; 546/170; 546/173; 546/174; 546/176; 546/177; 546/178
[58] Field of Search .................. 546/153-156, 546/168, 170, 173, 174, 176-180

[56] References Cited

U.S. PATENT DOCUMENTS 4,970,215  11/1990  Mohrs et al. .................. 514/311
5,091,392   2/1992  Raddatz et al. ................ 514/311

OTHER PUBLICATIONS

CA 113(9) 78180e, (1990).
CA 113(7) 58959n, (1989).
Chemical Abstracts Service 117:19908 (1992).
Fuji et al., "Binaphthol as a Chiral Auxiliary . . . ", Tetrahedron Letters, vol. 30, No. 21, (1989), pp. 2825-2828.
A. Guy et al., "Stereoselective Acetoxylation of Chiral . . . ", Tetrahedron Letters, vol. 30, No. 3, (1989), pp. 327-330.
A. Ando et al., "Asymmetric Synthesis using Chiral Bases . . . ", J. Chem. Soc., Chem. Commun. (1987), pp. 656-661.
M. Lemaire et al., "Asymmetric Control of Oxidation of Aromatic . . . ", J. Chem. Soc., Chem. Commun. (1986), pp. 741-742.
G. E. Jeromin et al., "Seitenkettenchlorierungen von N-heterocyclen . . . ", Chem. Ber. vol. 120 (1987), pp. 649-651.
Beilstein: Syst. No. 452, pp. 15, 29 and 43.

*Primary Examiner*—Marianne M. Cintins
*Assistant Examiner*—Catherine Scalzo
*Attorney, Agent, or Firm*—Sprung Horn Kramer & Woods

[57] ABSTRACT

(Quinolin-2-yl-methoxy)phenylacetic acids are known as inhibitors of enzymatic reactions in the context of arachidonic acid metabolism.

Enantiomerically pure (quinolin-2-yl-methoxy)phenylacetic acids can be prepared in a simple manner and in high purity and yield by diastereoselective alkylation of corresponding (quinolin-2-yl-methoxy)phenylacetic acid menthyl esters and subsequent specific removal of the ester radical with acids.

9 Claims, No Drawings

PROCESS FOR THE PREPARATION OF ENANTIOMERICALLY PURE SUBSTITUTED (QUINOLIN-2-YL-METHOXY)PHENYLACETIC ACIDS

The invention relates to a process for the preparation of enantiomerically pure (quinolin-2-yl-methoxy)-phenylacetic acids, some of which are known, which can be employed as inhibitors of enzymatic reactions in the context of arachidonic acid metabolism, in particular lipoxygenase.

It is already known from the literature that chiral 4-substituted phenylacetic acid esters are suitable for stereoselective acetoxylations and are employed in the asymmetrically controlled oxidation of aromatic compounds via a donor-acceptor interaction [cf. J. Chem. Soc., Chem. Commun. 1986, pp. 741–742; THL Vol. 30, No. 3, pp. 327–330, 1989].

It is also known that enantiomerically pure 4-(quinolin-2-yl-methoxy)phenylacetic acids can be separated into the corresponding enantiomers by diasteromeric separation by customary methods, for example by chromatography or fractional crystallisation [cf. DOS (German Published Specification) 3,916,663].

This process has several disadvantages: both the chromatographic diastereomer separation and the fractional crystallisation of the diastereomers is associated with great technical expenditure. Moreover, in this process, as a rule, fifty percent of the "wrong" diastereomer are obtained, which can then no longer be recycled in the original preparation process.

This fifty percent loss in yield impairs the economy of a (large) industrial process considerably, quite apart from the fact that fifty percent of "by-product" have to be disposed of. In addition, the customary chiral auxiliary reagents are generally very expensive even in small amounts and can then usually only be prepared via a complicated synthesis route.

It has now been found that enantiomerically pure (quinolin-2-yl-methoxy)phenylacetic acids of the general formula (I)

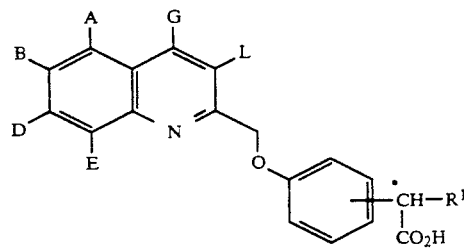

in which

A, B, D, E, G and L are identical or different and represent hydrogen, hydroxyl, halogen, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, and $R^1$ represents cycloalkyl having 4 to 12 carbon atoms, are obtained by a process in which compounds of the general formula (II)

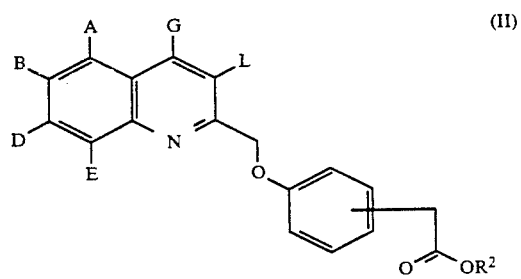

in which

A, B, D, E, G and L have the abovementioned meaning, and $R^2$ represents a chiral alcohol radical, are first converted with compounds of the general formula (III)

$$R^1-Y \qquad (III)$$

in which $R^1$ has the abovementioned meaning and

Y represents a typical leaving group such as, for example, bromine, chlorine, iodine, mesyl, tosyl or trifluoromethylsulphonyl, preferably iodine or bromine, by diastereoselective alkylation in inert solvents in the presence of a base into compounds of the general formula (IV)

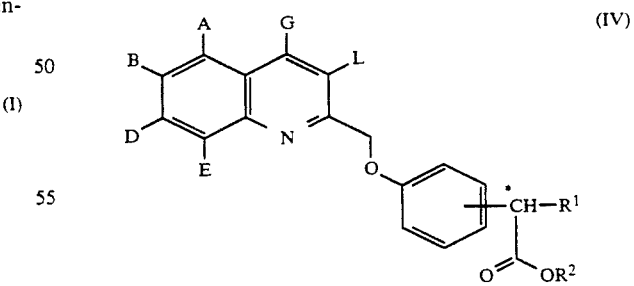

in which

A, B, D, E, G, L, $R^1$ and $R^2$ have the abovementioned meaning, and in a second step the radical $R^2$ is specifically removed with acids without racemisation.

The process according to the invention can be illustrated by way of example by the following equation:

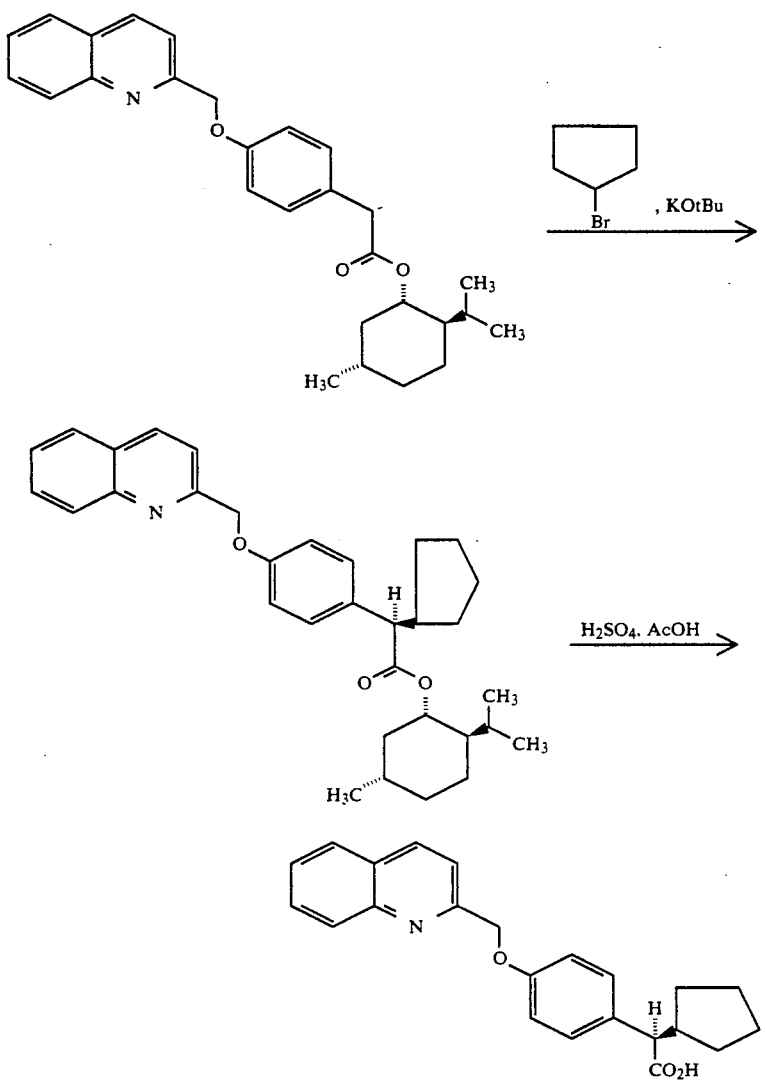

Surprisingly, the process according to the invention yields the desired enantiomerically pure (quinolin-2-yl-methoxy)phenylacetic acids in very good yields and in high purity without great technical expenditure.

Depending on the configuration of the radical $R^2$ and the steric effects of the alkyl halide (III) used, the alkylation of the compound (II) for the first time takes place diastereoselectively in high yields and in a simple manner. The compounds (IV) are obtained with a high diastereomer excess and crystallise from the reaction mixture directly, after which even simple crystallisation of the crude products yields the compounds of the formula (IV) in diastereomerically pure form.

A further advantage of the process according to the invention is that, by suitable choice of the solvent and of a base, the undesired diasteromer can be epimerised to the desired diastereomer, which in turn crystallises out directly. Thus, further (desired) diastereomerically pure product can be obtained from the mother liquors by repeated epimerisation and crystallisation. The entire process can be optimised in the form of a cyclic process by direct admixture of the mother liquors to the alkylation step.

A great advantage of the process according to the invention is furthermore that the starting compounds are very easily accessible. They can be prepared from relatively simple building blocks in good yields with low technical expenditure. Moreover, the process according to the invention enables existing amounts of known racemates of the compounds of the general formula (I) to be converted into the corresponding enantiomers. The process according to the invention enables the preparation of the compounds of the general formula (I) according to the invention with few synthesis steps and with a substantially higher total yield than with processes known from the prior art.

Formula (I) provides a general definition of the (quinolin-2-yl-methoxy)phenylacetic acids prepared by the process according to the invention. The corresponding salts can be obtained according to customary methods with bases.

$R^2$ in the context of the abovementioned definition represents a chiral alcohol radical such as, for example, (+)- or (−)-menthyl, (+)- or (−)-bornyl, (+)- or (−)-isobornyl or (−)-8-phenylmenthyl. $R^2$ preferably represents (+)- or (−)-menthyl.

Enantiomerically pure (quinolin-2-yl-methoxy)-phenylacetic acids of the general formula (I) preferably prepared by the process according to the invention are those in which A, B, D, E, G and L are identical or different and represent hydrogen, fluorine, chlorine, bromine, trifluoromethyl or represent straight-chain or branched alkyl having up to 6 carbon atoms and $R^1$ represents cyclopentyl, cyclohexyl, cycloheptyl or cyclooctyl.

(Quinolin-2-yl-methoxy)phenylacetic acids of the general formula (I) particularly preferably prepared by the process according to the invention are those in which A, B, D, E, G and L represent hydrogen and $R^1$ represents cyclopentyl, cyclohexyl or cycloheptyl.

(Quinolin-2-yl-methoxy)phenylacetic acids of the general formula (I) very particularly preferably prepared by the process according to the invention are those in which A, B, D, E, G and L represent hydrogen and the radical *CH—$R^1$—$CO_2H$ is the 4-position to the quinolylmethoxy radical.

Suitable solvents for the alkylation are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Dimethylformamide is preferred.

The alkylation is carried out at normal pressure in the abovementioned solvents, if appropriate under a protective gas atmosphere, at temperatures from −20° C. to +100° C., preferably at −10° C. to +30° C.

Suitable bases for the diastereoselective alkylation are the customary basic compounds. These include alkali metal hydrides such as sodium hydride, alkali metal amides such as sodium amide, alkali metal alkoxides such as sodium methoxide, sodium ethoxide, potassium methoxide, potassium ethoxide or potassium tert-butoxide, or organic amines such as trialkylamines, for example triethylamine, or organolithium compounds such as butyllithium or phenyllithium. Potassium tert-butoxide is preferred.

In the diastereoselective alkylation, the base is employed in an amount from 1 mol to 10 mol, preferably from 1.2 mol to 3 mol, relative to 1 mol of the compounds of the general formula (II).

The customary organic carboxylic acids, such as, for example, acetic acid or formic acid, or inorganic acids such as, for example, hydrobromic acid, hydrochloric acid or sulphuric acid or mixtures of the acids mentioned are suitable for the removal of the chiral radical $R^2$. Acetic acid, formic acid, hydrobromic acid and/or sulphuric acid are preferred. The mixture acetic acid/sulphuric acid and also formic acid/hydrobromic acid and formic acid/sulphuric acid is very particularly preferred.

The acids or their mixtures are used simultaneously as the solvent and are thus employed in a large excess.

Removal is carried out in a temperature range from 0° C. to +150° C., preferably from 40° C. to 100° C.

It can in general be carried out at normal pressure, but if appropriate also at elevated or reduced pressure (for example 0.5 to 3 bar).

After neutralisation with bases in water or in one of the abovementioned solvents, in particular in a water/toluene mixture, the acids are worked up by a customary method.

Suitable bases for the neutralisation are alkali metal hydroxides such as sodium hydroxide or potassium hydroxide. Sodium hydroxide is preferred.

The enantiomerically pure crude products of the general formula (I) are purified by a customary method, for example by washing in one of the abovementioned solvents, preferably isopropanol or by chromatography on silica gel.

The enantiomerically pure compounds of the general formula (I) are known in principle from DOS (German Published Specification) 3,916,663 and are useful active compounds for the production of medicaments, in particular lipoxygenase inhibitors.

The starting compounds of the formula (II) are new and are prepared by etherifying hydroxyphenylacetic acid derivatives of the general formula (V)

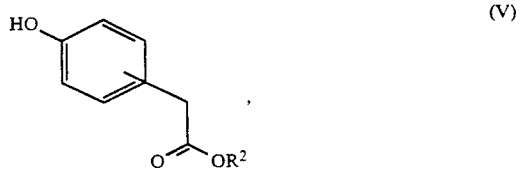

(V)

in which $R^2$ represents a chiral alcohol radical, with halogenomethylquinolines of the general formula VI

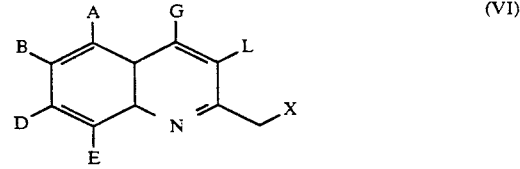

(VI)

in which

A, B, D, E, G and L have the abovementioned meaning and

X represents halogen, preferably chlorine, in inert solvents, if appropriate in the presence of a base and/or of an auxiliary, or under phase transfer catalysis.

The preparation can be illustrated by way of example by the following equation:

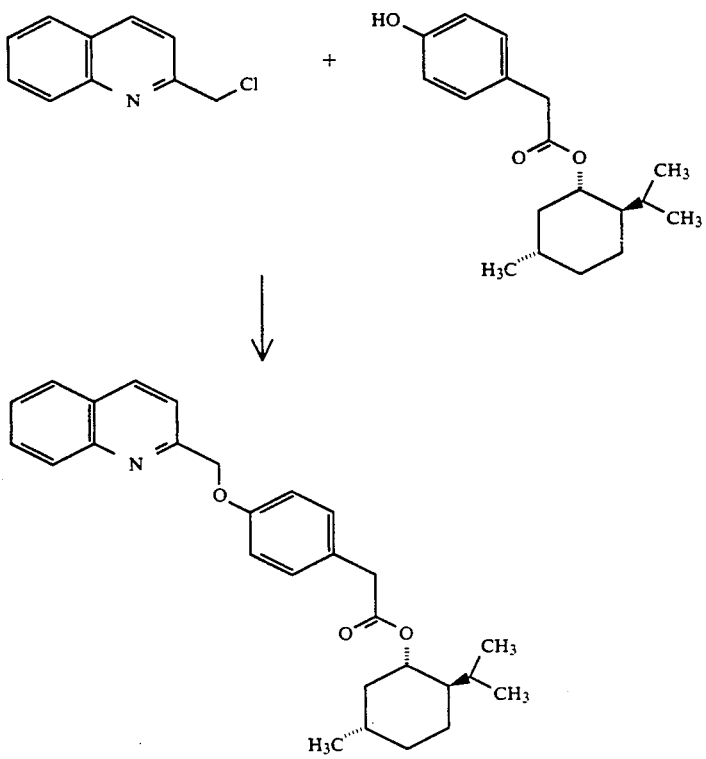

The etherification can be carried out in inert organic solvents, if appropriate in the presence of a base. Solvents for the etherification can be inert organic solvents which do not change under the reaction conditions. These preferably include alcohols such as ethanol, propanol or isopropanol, ethers such as, for example, dioxane, tetrahydrofuran or diethyl ether, halogenohydrocarbons such as dichloromethane, trichloromethane, tetrachloromethane, 1,2-dichloroethane or trichloroethylene, hydrocarbons such as benzene, xylene, toluene, hexane, cyclohexane or mineral oil fractions, nitromethane, dimethylformamide, acetonitrile, acetone or hexamethylphosphoric triamide. It is also possible to employ mixtures of the solvents. Methylene chloride and isopropanol are preferred.

Bases which can be employed for the etherification are inorganic or organic bases. These preferably include alkali metal carbonates such as sodium carbonate or potassium carbonate, alkaline earth metal carbonates such as calcium carbonate, or organic amines (trialkyl($C_1$-$C_6$)amines) such as triethylamine, or heterocycles such as pyridine, methylpiperidine, piperidine or morpholine. Bases which can also be employed are hydrides, such as sodium hydride. To activate the halide (III) employed, it is also possible to add alkali metal iodides, preferably potassium iodide, to the reaction solution.

The etherification is in general carried out in a temperature range from 0° C. to +150° C., preferably from +10° C. to +100° C.

The etherification is in general carried out at normal pressure. However, it is also possible to carry out the process at reduced pressure or elevated pressure (for example in a range from 0.5 to 5 bar).

In general, 0.5 to 5, preferably 1 to 2, mol of halide (III) are employed, relative to 1 mol of the reaction component. The base is in general employed in an amount from 0.5 to 5 mol, preferably from 1 to 3 mol, relative to the halide.

The phase transfer catalysis is in general carried out in one of the abovementioned solvents, preferably in dimethylformamide, methylene chloride or toluene, using crown ethers or quaternary ammonium salts, preferably using tetrabutylammonium iodide.

The compounds of the general formula (IV) are known per se or can be prepared by a customary method [cf. Chem. Ber. 120, 649 (1987)].

The compounds of the general formula (III) are known [cf. Beilstein 5,19/5,24/5,29] or can be prepared from the corresponding alcohols or cycloalkenes by customary methods.

The compounds of the general formula (VI) having the free OH function are for the major part new and can be prepared, for example, from the known protected derivatives (O—CH($CH_3$)$_2$) by removal of the protective group by customary methods (cf. THL, Vol. 30, No. 3, pp. 327-330 and J. Chem. Soc., Chem. Commun., 1986, pp. 741-742).

In the context of the process according to the invention, the compounds of the general formula (V) are reacted with the appropriate chiral alcohol in toluene and in the presence of p-toluenesulphonic acid, it being possible to suppress side reactions nearly completely by an excess of the alcohol.

The chiral alcohol is employed in an amount from 0.5 to 10 mol, preferably from 1 mol to 3 mol, relative to the free p-hydroxyphenylacetic acid.

The chiral alcohol, in particular (+)- and (−)-menthyl, is reasonably priced and commercially available in large amounts.

The following examples serve to clarify the invention without additionally restricting it.

PREPARATION EXAMPLES

Example 1

(+)-Menthyl 4-hydroxyphenylacetate

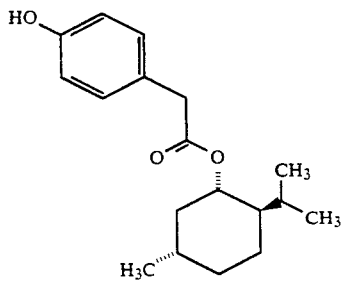

2.9 kg of p-hydroxyphenylacetic acid and 1.95 kg of (+)-menthol are heated to boiling for 16 hours with 40 g of p-toluenesulphonic acid in 25 l of toluene; about 300 ml of water are separated in this process. The toluene solution is washed with 10 l of saturated NaHCO$_3$ solution and 10 l of water and concentrated to dryness in vacuo. The title compound is obtained as 5.4 kg of oily residue (98–100% of theory) having a purity of 91.8% (HPLC surface area percentage). For analytical purposes, the (+)-menthylhydroxyphenylacetate was recrystallised twice from n-hexane.

M.p.: 50°–51° C.
Rotation: $\alpha_D^{20} = 63.3$ (c=1, CHCl$_3$)

Example 2

(+)-Menthyl 4-(quinolin-2-yl-methoxy) phenylacetate

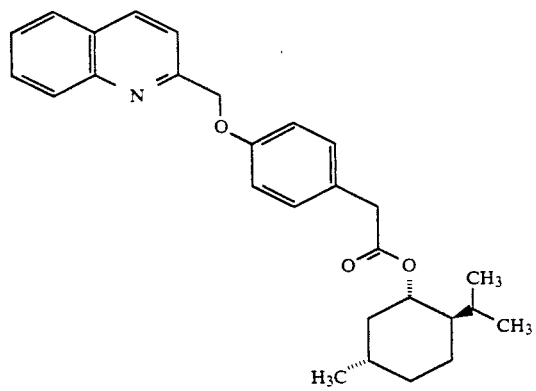

5.4 kg of the compound from Example 1, 28.7 kg of quinaldine chloride, 3.87 kg of potassium carbonate and 400 g of potassium iodide are reacted in 18 l of boiling isopropanol for 20 hours. The title compound is precipitated by addition of 19 l of water. The crystallisate is centrifuged and washed with 10 l of isopropanol/water 1:1 and 8 l of water.

Yield: 5.44 kg (78% of theory).
Purity according to HPLC: 99.5%
M.p.: 86° C.
Rotation: $\alpha_D^{20} = 45.0$ (c=1, CHCl$_3$)

Example 3

(+)-Menthyl (2R)-2-[4-(quinolin-2-yl-methoxy)phenyl]-2-cyclopentylacetate

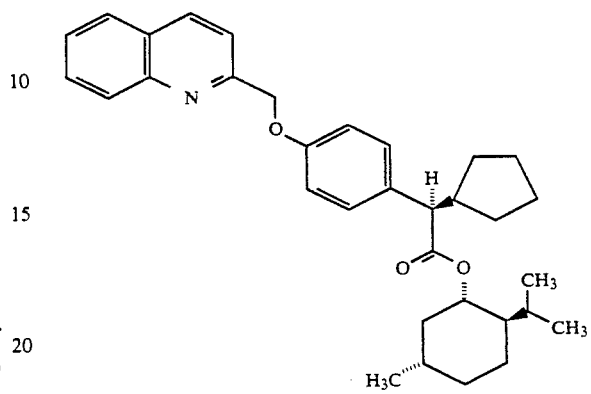

A solution of 1.87 kg of potassium tert-butoxide in 5 l of DMF is added between −5° C. and +5° C. to a solution of 5.44 kg of the compound from Example 2 and 2.06 kg of bromocyclopentane in 8.5 l of dimethylformamide under a protective gas atmosphere. The mixture is subsequently stirred at −5° C. for 4 hours and 18.5 l of water are then added. The crude product is centrifuged off, dried in vacuo at 60° C. for 24 hours and recrystallised twice from 7.5 l of ligroin; the hot ligroin solution is filtered in the first recrystallisation.

Yield: 4.8 kg (76% of theory)
Purity according to HPLC: 99.7%
Diastereomer excess: 99.5%
M.p.: 124° C.
Rotation: $\alpha_D^{20} = 26.6$ (c=1, CHCl$_3$)

Example 4

(2R)-2-[4(Quinolin-2-yl-methoxy)phenyl]-2-cyclopentylacetic acid

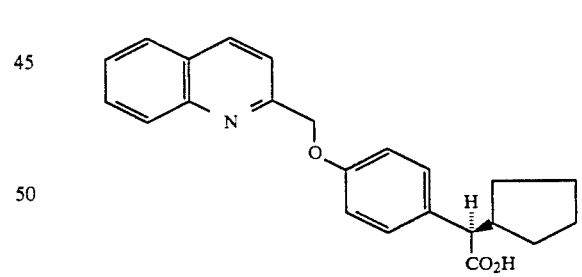

2.4 kg of the compound from Example 3 are hydrolysed for 4 hours in a boiling mixture of 1 l of concentrated sulphuric acid and 5.6 l of glacial acetic acid. The mixture is cooled, 2 l of toluene are added and it is slowly allows to flow into 15 l of water and 6 l of toluene, it being neutralised at the same time by addition of about 1.7 l of 45% strength sodium hydroxide solution. The title compound precipitating in this process is centrifuged off and recrystallised from 8 l of isopropanol.

Yield: 13.1 kg (75% of theory)
Purity according to HPLC: 99.9%
Enantiomer excess: 99.4%
M.p.: 170°–171° C.
Rotation: $\alpha_D^{20} = -41.2$ (c=1, CHCl$_3$)

Example 5

(−)-Menthyl hydroxyphenylacetate

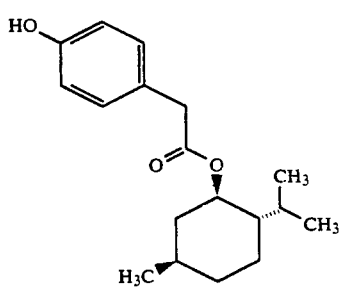

2.1 kg of hydroxyphenylacetic acid are esterified with 2.5 kg of (−)-menthol in 15 l of boiling toluene with the addition of 40 g of toluenesulphonic acid; the water of reaction is removed from circulation in a water separator. When water is no longer separated, the mixture is cooled, washed with 4 l of saturated NaHCO$_3$ and twice with 4 l of water and concentrated to dryness in vacuo. The title compound is obtained as an oily residue.

Yield: 40.2 kg (100% of theory)
Purity according to HPLC: 95%
M.p.: 50°–51° C.
Rotation: $\alpha^{20}_D = -62.5$ (c=1, CHCl$_3$)

Example 6

(−)-Menthyl 4-(quinolin-2-yl-methoxy)phenylacetate

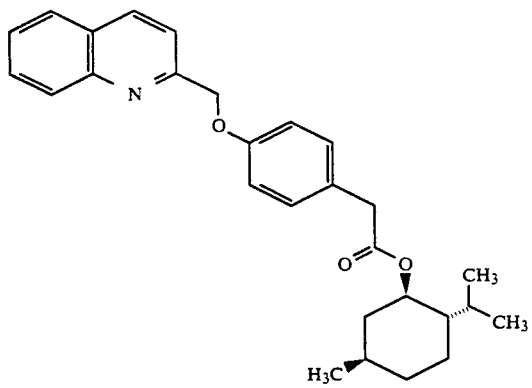

4.14 kg of the compound from Example 5 are stirred in 15 l of DMF for 4 hours at 50° C. with 2.48 kg of quinaldine chloride, 2.94 kg of potassium carbonate, 150 g of potassium iodide and 150 g of tetrabutylammonium iodide. The salts are then filtered off and washed with 6 l of isopropanol. 2.5 l of water are added to the filtrate, during the course of which the title compound crystallises out. It is centrifuged off, washed with 8 l of isopropanol/water 1:1 and with 6 l of water and dried in vacuo at 50° C.

Yield: 5.42 kg (88% of theory)
Purity according to HPLC: 99%
M.p.: 86° C.
Rotation: $\alpha_D^{20} = -44.0$ (c=1, CHCl$_3$)

Example 7

(−)-Menthyl (2R)-2-[4-(quinolin-2-yl-methoxy)phenyl]-2-cycloheptylacetate

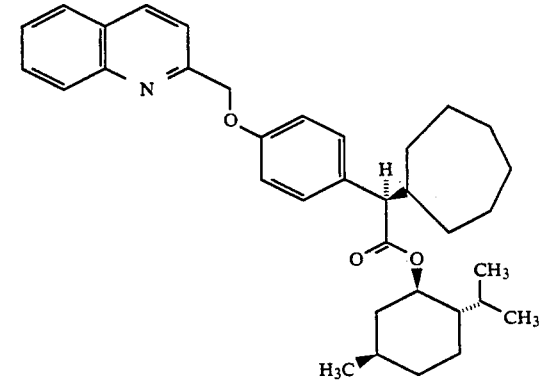

1.3 kg of the compound from Example 6 are stirred with exclusion of moisture at −5° C. to +5° C. with 580 g of bromocycloheptane in 2.4 l of DMF. During the course of about 2 hours, a solution of 400 g of potassium tert-butoxide in 1.6 l of DMF is added. The mixture is stirred for a further 4 hours between −20° C. and −10° C. and 7.5 l of water are then added, during the course of which the title compound precipitates as a crude product. The crude product is centrifuged off, dried at 50° C. in vacuo and recrystallised twice using 6 l of ligroin; the solution is filtered hot in the first recrystallisation.

Yield: 1.02 kg (64% of theory)
Purity according to HPLC: >99%
Diastereomer excess: >99%
M.p.: 127° C.
Rotation: $\alpha_D^{20} = -44.3$ (c=1, CH$_2$Cl$_2$)

Example 8

(2R)-2-[4-Quinolin-2-yl-methoxy)phenyl]-2-cycloheptylacetic acid

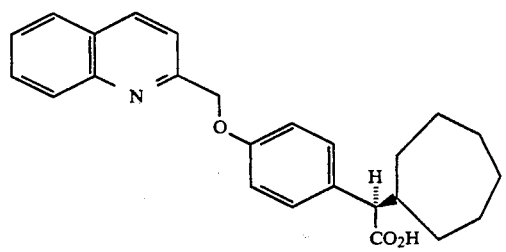

1 kg of the compound from Example 7 is stirred for 3 to 4 hours in a boiling mixture of 9 l of 98% strength formic acid and 0.8 l of 48% strength hydrobromic acid. A light phase separating in the distillate is separated off during the course of this. The reaction solution is cooled and added to a mixture of 750 ml of 45% strength sodium hydroxide solution, 7.5 l of water and 2 l of isopropanol. The crude product precipitating during the course of this is centrifuged off and recrystallised from a mixture of 3.6 l of isopropanol and 1.2 l of water.

Yield: 624 g (85% of theory)

Purity according to HPLC: >99%
Enantiomer excess: >99.5%
M.p.: 170°-172° C.
Rotation: $a_D^{20} = -27.5$ (c=1, CH$_2$Cl$_2$)

What is claimed is:

1. A process for the preparation of an enantiomerically pure (quinolin-2-yl-methoxy)phenylacetic acid of the formula

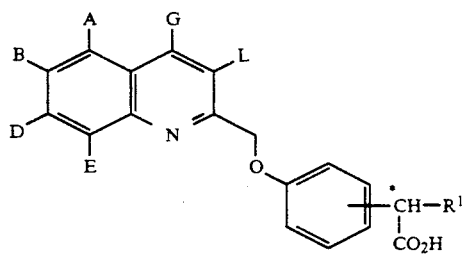
(I)

in which
A, B, D, E, G and L are identical or different and represent hydrogen, hydroxyl, halogen, carboxyl, nitro, trifluoromethyl, trifluoromethoxy or alkoxy each having up to 8 carbon atoms, or represent phenyl or naphthyl which is optionally substituted by halogen, hydroxyl, nitro or cyano,
and
R$^1$ represents cycloalkyl having 4 to 8 carbon atoms, which comprises alkylating a compound of the formula

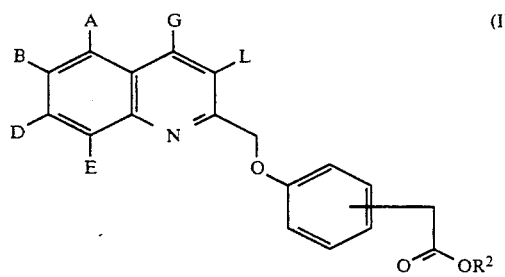
(II)

in which
R$^2$ represents a chiral alcohol radical selected from the group consisting of (+)- or (−)-menthyl, (+)- or (−)-bornyl, (+)- or (−)-isobornyl and (−)-8-phenylmenthyl,
with a compound of the formula

R$^1$—Y (III)

in which
Y represents a leaving group,
in an inert solvent in the presence of a base to form a compound of the formula

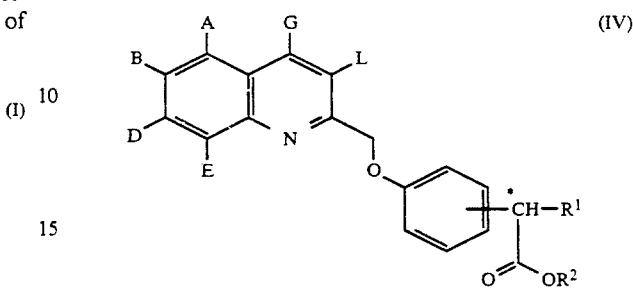
(IV)

and in a second step specifically removing the radical R$^2$ with an acid without racemisation.

2. The process according to claim 1 in which
A, B, D, E, G and L are identical or different and represent hydrogen, fluorine, chlorine, bromine, trifluoromethyl or
represent straight-chain or branched alkyl having up to 6 carbon atoms,
and
R$^1$ represents cyclopentyl, cyclohexyl, cycloheptyl or cyclooctyl.

3. The process according to claim 1 in which
A, B, D, E, and L represent hydrogen, and
R$^1$ represents cyclopentyl, cyclohexyl or cycloheptyl.

4. The process of claim 3, wherein R$^1$ represents cyclopentyl, R$^2$ represents menthyl and end product (I) is 2R.

5. The process according to claim 1, in which R$^2$ is (+)- or (−)-menthyl.

6. The process according to claim 1, wherein the base in the alkylation is an alkali metal hydride, alkali metal amide, alkali metal alkoxide, organic amine or organolithium compound.

7. The process according to claim 1, wherein the acid for the removal of R$^2$ is at least one of acetic acid, formic acid, hydrobromic acid and sulphuric acid.

8. The process according to claim 1, wherein Y is a member selected from the group consisting of bromine, chlorine, iodine, mesyl, tosyl and trifluoromethylsulphonyl.

9. The process according to claim 1, wherein Y is iodine or bromine.

* * * * *

UNITED STATES PATENT AND TRADEMARK OFFICE
CERTIFICATE OF CORRECTION

PATENT NO : 5,306,820
DATED : April 26, 1994
INVENTOR(S): Matthias Decker, et al.

It is certified that error appears in the above-identified patent and that said Letters Patent is hereby corrected as shown below:

Col. 13, Line 24    After "trifluoromethoxy" insert --or represent straight-chain or branched alkyl--

Signed and Sealed this

Seventh Day of December, 1999

Attest:

Q. TODD DICKINSON

*Attesting Officer*    Acting Commissioner of Patents and Trademarks